(12) United States Patent
Zhang et al.

(10) Patent No.: US 7,774,061 B2
(45) Date of Patent: Aug. 10, 2010

(54) IMPLANTABLE CARDIAC DEVICE WITH ISCHEMIA RESPONSE CAPABILITY

(75) Inventors: Yi Zhang, Blaine, MN (US); Aaron McCabe, Minneapolis, MN (US); Kevin J. Stalsberg, White Bear Lake, MN (US); Kent Lee, Shoreview, MN (US); Marina V. Brockway, Shoreview, MN (US); Joseph M. Pastore, Woodbury, MN (US); Allan C. Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 593 days.

(21) Appl. No.: 11/318,257

(22) Filed: Dec. 23, 2005

(65) Prior Publication Data

US 2007/0150015 A1  Jun. 28, 2007

(51) Int. Cl.
*A61N 1/37* (2006.01)

(52) U.S. Cl. .............................. 607/9; 607/17; 607/18

(58) Field of Classification Search .................... 607/9, 607/17, 18, 19
See application file for complete search history.

(56) References Cited

U.S. PATENT DOCUMENTS

| 3,799,147 | A | 3/1974 | Adolph et al. |
|---|---|---|---|
| 4,432,374 | A | 2/1984 | Osanai |
| 4,492,753 | A | 1/1985 | Shell et al. |
| 4,798,211 | A | 1/1989 | Goor et al. |
| 4,821,735 | A | 4/1989 | Goor et al. |
| 5,199,428 | A | 4/1993 | Obel et al. |
| 5,228,449 | A | 7/1993 | Christ et al. |
| 6,021,350 | A | 2/2000 | Mathson |
| 6,233,486 | B1 | 5/2001 | Ekwall et al. |
| 6,256,538 | B1 | 7/2001 | Ekwall |
| 6,285,907 | B1 | 9/2001 | Kramer et al. |
| 6,319,205 | B1 | 11/2001 | Goor et al. |
| 6,361,522 | B1 | 3/2002 | Scheiner et al. |
| 6,368,284 | B1 | 4/2002 | Bardy |
| 6,381,493 | B1 * | 4/2002 | Stadler et al. .................. 607/9 |
| 6,468,263 | B1 | 10/2002 | Fischell et al. |
| 6,522,922 | B1 * | 2/2003 | Perschbacher et al. ......... 607/9 |
| 6,604,000 | B2 | 8/2003 | Lu |
| 6,609,023 | B1 | 8/2003 | Fischell et al. |
| 6,750,030 | B2 | 6/2004 | Kleinfeld |
| 6,827,690 | B2 | 12/2004 | Bardy |
| 6,937,899 | B2 | 8/2005 | Sheldon et al. |
| 7,039,462 | B2 | 5/2006 | Pastore et al. |

(Continued)

OTHER PUBLICATIONS

Bernier, M., et al., "Ischemia-induced and reperfusion-induced arrhythmias: importance of heart rate.", *American Journal of Physiology. Heart and Circulatory Physiology*, 256(1 Pt 2), (Jan. 1989), H21-31.

(Continued)

*Primary Examiner*—Scott M Getzow
*Assistant Examiner*—Joseph M Dietrich
(74) *Attorney, Agent, or Firm*—Schwegman, Lundberg & Woessner, P.A.

(57) ABSTRACT

A cardiac device is described with the capability of detecting cardiac ischemia using multiple sensing modalities. The device may be configured to modify its behavior in delivering therapies to treat bradycardia or tachyarrhythmias in response to detection of cardiac ischemia.

39 Claims, 5 Drawing Sheets

U.S. PATENT DOCUMENTS

| | | | |
|---|---|---|---|
| 7,171,258 B2 | 1/2007 | Goode | |
| 7,181,268 B2 | 2/2007 | Sheldon et al. | |
| 7,190,996 B2 | 3/2007 | Jarverud | |
| 7,215,997 B2 | 5/2007 | Yu et al. | |
| 7,299,087 B2 | 11/2007 | Bardy | |
| 7,479,112 B2 | 1/2009 | Sweeney et al. | |
| 7,539,533 B2 | 5/2009 | Tran | |
| 7,577,478 B1 | 8/2009 | Kroll et al. | |
| 2002/0111551 A1 | 8/2002 | Van Erlach et al. | |
| 2003/0004549 A1 | 1/2003 | Hill et al. | |
| 2003/0060854 A1* | 3/2003 | Zhu | 607/25 |
| 2003/0083582 A1* | 5/2003 | Hirsh | 600/509 |
| 2004/0122478 A1* | 6/2004 | Stadler et al. | 607/17 |
| 2004/0133247 A1 | 7/2004 | Stahmann et al. | |
| 2005/0043675 A1 | 2/2005 | Pastore et al. | |
| 2005/0283195 A1 | 12/2005 | Pastore et al. | |
| 2005/0288721 A1 | 12/2005 | Girouard et al. | |
| 2006/0009811 A1 | 1/2006 | Sheldon et al. | |
| 2006/0025824 A1* | 2/2006 | Freeman et al. | 607/5 |
| 2006/0259087 A1 | 11/2006 | Baynham et al. | |
| 2006/0282000 A1 | 12/2006 | Zhang et al. | |
| 2006/0287684 A1 | 12/2006 | Baynham et al. | |
| 2007/0043393 A1 | 2/2007 | Brockway et al. | |
| 2007/0049835 A1 | 3/2007 | Goode | |
| 2007/0054871 A1 | 3/2007 | Pastore et al. | |
| 2007/0150005 A1 | 6/2007 | Sih et al. | |
| 2007/0162081 A1 | 7/2007 | Yu et al. | |
| 2007/0276453 A1 | 11/2007 | Hill et al. | |
| 2007/0299356 A1 | 12/2007 | Wariar et al. | |
| 2008/0058661 A1 | 3/2008 | Bardy | |
| 2008/0081354 A1 | 4/2008 | Qu et al. | |
| 2008/0091138 A1 | 4/2008 | Pastore et al. | |
| 2008/0177156 A1 | 7/2008 | Zhang et al. | |
| 2008/0177191 A1 | 7/2008 | Patangay et al. | |
| 2008/0177194 A1 | 7/2008 | Zhang et al. | |
| 2008/0183062 A1 | 7/2008 | Hazui et al. | |
| 2008/0228094 A1 | 9/2008 | Audet et al. | |
| 2008/0287818 A1 | 11/2008 | Shelchuk et al. | |
| 2008/0312519 A1 | 12/2008 | Maschke | |
| 2009/0025459 A1 | 1/2009 | Zhang et al. | |
| 2009/0082781 A1 | 3/2009 | Tran et al. | |
| 2009/0124916 A1 | 5/2009 | Sweeney et al. | |
| 2009/0137890 A1 | 5/2009 | Burnes et al. | |
| 2009/0171228 A1 | 7/2009 | Fischell et al. | |

OTHER PUBLICATIONS

Lunati, et al., "Ventricular arrhythmias developed by ischemic and non-ischemic heart failure patients implanted with bi-ventricular cardioverter-defibrillators for primary or secondary prevention: the InSync ICD Italian Registry", *NASPE 2004*, (2004), 1 pg.

* cited by examiner

IMPLANTABLE CARDIAC DEVICE WITH ISCHEMIA RESPONSE CAPABILITY

FIELD OF THE INVENTION

The present disclosure pertains to systems and methods for cardiac rhythm management. In particular, the present disclosure relates to cardiac pacemakers and their methods of operation.

BACKGROUND

Implantable cardiac rhythm management devices that provide electrical stimulation to selected chambers of the heart have been developed in order to treat a number of cardiac disorders. A pacemaker, for example, is a device which paces the heart with timed pacing pulses, most commonly for the treatment of bradycardia where the ventricular rate is too slow. Atrio-ventricular conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Pacemakers have also been developed that provide appropriately timed electrical stimulation to one or more heart chambers in an attempt to improve the coordination of atrial and/or ventricular contractions, termed cardiac resynchronization therapy (CRT). Currently, a most common form of CRT applies stimulation pulses in either a left ventricle-only pacing mode or a biventricular pacing mode, where the pace or paces are delivered in conjunction with a bradycardia pacing mode. Implantable devices may also be used to treat cardiac rhythms that are too fast, with either anti-tachycardia pacing or the delivery of electrical shocks to terminate atrial or ventricular fibrillation by implantable cardioverter/defibrillator (ICD). The term "pacemaker" as used herein, should be taken to mean any device with a pacing functionality, such as an ICD with a pacemaker incorporated therein.

SUMMARY

Patients in whom cardiac devices are implanted are apt to suffer from some degree of coronary disease that may compromise blood flow to the heart. The present disclosure relates to an implantable cardiac device that is configured to detect cardiac ischemia and then respond appropriately by modifying its behavior in delivering one or more therapies to the patient. In particular embodiments, an implantable cardiac device for delivering therapy to the heart in the form of bradycardia pacing, CRT, and/or anti-tachyarrhythmia therapy is equipped with one or more sensing modalities for detecting cardiac ischemia.

Cardiac ischemia may be detected by finding changes in measurable parameters related to cardiac ischemia. For example, cardiac ischemia may be present if a current of injury is detected in an electrogram or subcutaneous electrocardiogram (ECG) recorded from the device's sensing channels, an elevated level of one or more cardiac enzymes is detected via a chemosensor, abnormal heart wall movement is detected via an ultrasonic sensor, abnormal heart sounds are detected via an acoustic sensor, increased sympathetic nervous activity is detected via an analysis of heart rate variability, and/or changes in cardiac output or pressure are detected via sensors for measuring cardiac impedance, blood flow, or blood pressure. A plurality of such ischemia parameter values may be employed to compute a composite ischemia function that can be used to detect cardiac ischemia. In one embodiment, the composite ischemia function is a numerically-valued function that is compared with a specified threshold value to ascertain whether or not cardiac ischemia is present. In another embodiment, the composite ischemia function is a vector-valued function that allows cardiac ischemia to not only be detected but also to be characterized in accordance with the particular combination of measurable ischemia parameter values making up the composite ischemia function. For example, multiple threshold values for the individual components of the composite ischemia function vector may be used to detect that cardiac ischemia is present and to further characterize the ischemia as to type or severity. When cardiac ischemia is detected and/or characterized, the event may then be logged as a clinically significant event and the recorded electrogram later downloaded to a clinician for analysis via an external programmer. The implantable device may also be configured to transmit an alarm message over a wireless telemetry link to a remote monitoring unit that relays the alarm to a patient management server via a network.

The operating behavior of the device may also be adjusted when cardiac ischemia is detected and/or characterized. For example, in atrial tracking pacing modes, the maximum tracking rate can be decreased so that the ventricles are paced at that rate even if the intrinsic atrial rate is higher. The lower rate limit or pacing modes that influence the lower rate limit (e.g., ventricular rate regularization, rate smoothing, rate adaptive pacing) can also be adapted to minimize myocardial oxygen consumption. In rate-adaptive pacing modes, where an escape interval for pacing a heart chamber is adjusted in order to pace the chamber at a sensor-indicated rate based upon a sensed exertion level, the maximum allowable sensor-indicated rate can be decreased. Rate-adaptive pacing could be discontinued or the response factor of the rate response curve (or response factors in the case of a multiple slope or non-linear rate response curve) used for rate-adaptive pacing can also be adjusted to map a given exertion level to a lower sensor-indicated rate if cardiac ischemia is detected. The device could also be configured to switch to a ventricular pacing mode that encourages intrinsic rather than paced ventricular beats such as a mode incorporating hysteresis or to switch to a non-ventricular pacing mode such as AAI. The device may also shorten the AV delay interval used to deliver ventricular pacing in order to lengthen ventricular diastole and increase coronary perfusion. A device configured to deliver anti-tachyarrhythmia therapy may modify the manner in which it delivers anti-tachycardia pacing (ATP) therapy versus shock therapy and/or modify ATP parameters such as rate or pacing vector. The implantable device may also be equipped with drug delivery capability so that a dose of medication (e.g., a thrombolytic) is delivered when cardiac ischemia is detected.

DETAILED DESCRIPTION

An implantable cardiac device with an ischemia response capability as described herein comprises one or more sensing modalities to detect changes in measurable or detectable parameters related to transient cardiac ischemia, referred to as ischemia parameters. Such changes may be electrophysiological, hemodynamic, mechanical, or chemical. The device may then employ algorithms to determine whether the ischemia parameter changes reflect cardiac ischemia such as computing a composite ischemia function to which a plurality of parameters are mapped. The composite ischemia function may be a numerically-valued function that is compared with a specified threshold in order to detect cardiac ischemia or a vector-valued function whose components are compared with multiple specified threshold values in order to both detect and characterize cardiac ischemia. The device may be further configured to characterize the parameter changes by tracking their time progression, and the composite ischemia function may be a function of both a plurality of ischemia parameter values and of the times at which the ischemia parameter values were measured or otherwise collected. The device may also be configured to change its operating behavior in various ways when cardiac ischemia is detected. In an embodiment in which cardiac ischemia is both detected and further characterized with a vector-valued composite ischemia function, the device may change its operating behavior in accordance with the characterization of the cardiac ischemia. Set forth below is a description of an exemplary implantable device that is equipped with various features, any or all or which may be incorporated into a device that implements the inventions as described herein. Detailed descriptions of methods and devices for detecting ischemia and for modifying the operating behavior of the device are also given.

1. Exemplary Hardware

Cardiac rhythm management devices such as pacemakers and ICDs are typically implanted subcutaneously on a patient's chest and have leads threaded intravenously into the heart to connect the device to electrodes used for sensing and delivery of electrical stimulation such as defibrillation shocks and pacing pulses. A programmable electronic controller causes the delivery of pacing pulses in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause a contraction in the absence of an intrinsic beat, a pacing pulse (either an atrial pace or a ventricular pace) with energy above the capture threshold can be delivered to the chamber.

Figure 1:
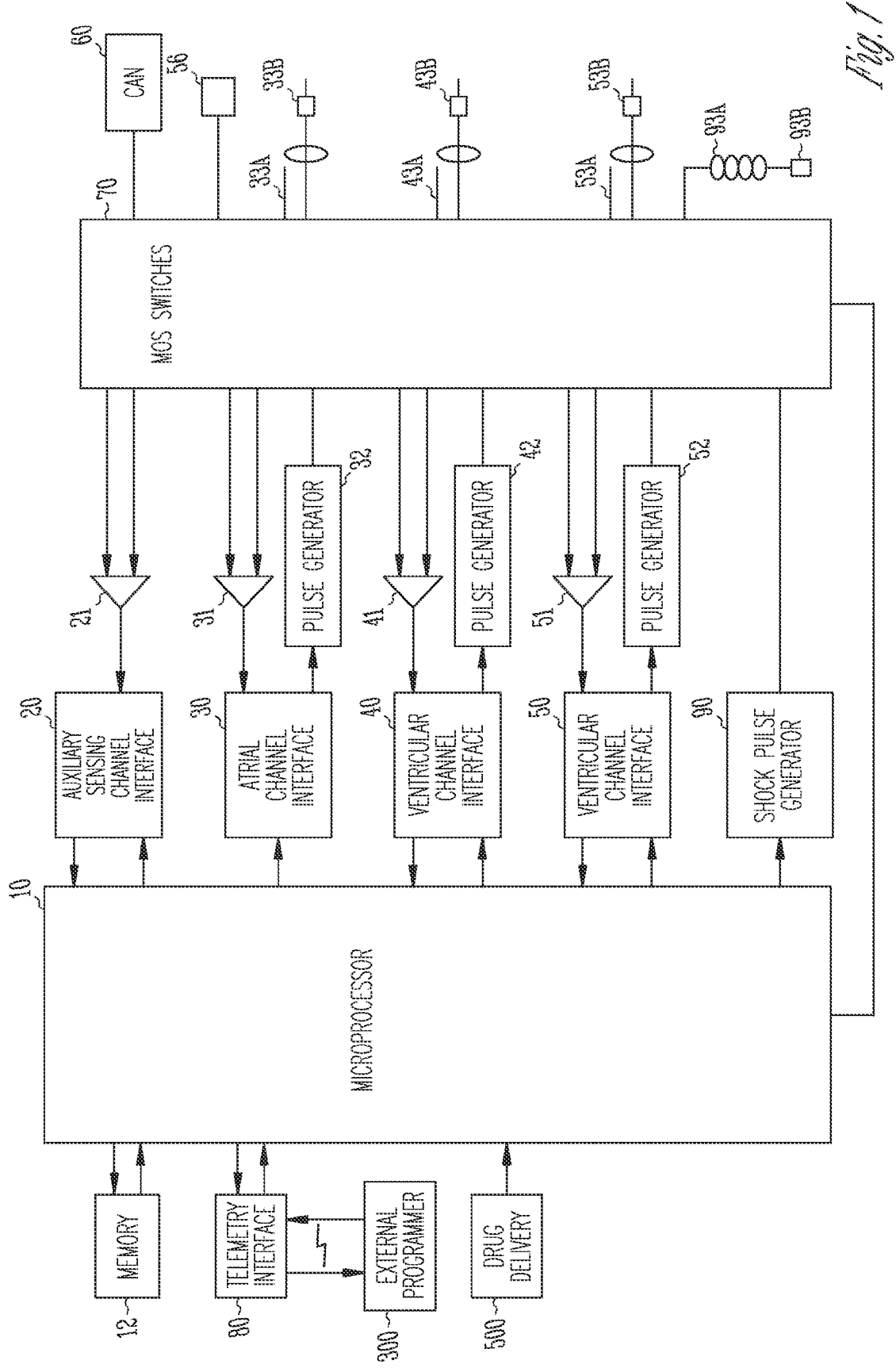
FIG. 1 is a block diagram of an exemplary cardiac rhythm management device.

A system diagram of an exemplary cardiac rhythm management device that may be configured to deliver conventional cardiac pacing, cardiac resynchronization therapy, and/ or anti-tachyarrhythmia therapy such as ATP and shock therapy is illustrated in FIG. 1. The controller of the device is made up of a microprocessor 10 communicating with a memory 12, where the memory 12 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the device in a number of programmed modes where a programmed mode defines how pacing pulses are output in response to sensed events and expiration of time intervals. A telemetry interface 80 is provided for communicating with an external device 300 over a wireless telemetry link. The external device may be a programmer which is a computerized device that can interrogate the device and receive stored data as well as adjust various operating parameters or may be a remote monitoring unit that relays data received from the implantable device to a patient management server via a network.

The device has an atrial sensing/pacing channel comprising ring electrode 33a, tip electrode 33b, sense amplifier 31, pulse generator 32, and an atrial channel interface 30 which communicates bidirectionally with a port of microprocessor 10. The device also has ventricular sensing/pacing channels that similarly include ring electrodes 43a and 53a, tip electrodes 43b and 53b, sense amplifiers 41 and 51, pulse generators 42 and 52, and ventricular channel interfaces 40 and 50. For each channel, the electrodes are connected to the pacemaker by a lead and used for both sensing and pacing. A switching network 70 (e.g., a MOS (metal-oxide-silicon) network) controlled by the microprocessor is used to switch the electrodes from the input of a sense amplifier to the output of a pulse generator. The device also includes a shock pulse generator 90 interfaced to the controller and a shock lead which incorporates a tip electrode 93b and a coil electrode 93a. Coil electrodes can be used to deliver pacing pulses but are designed especially for delivering cardioversion/defibrillation shocks. The shock lead would normally be disposed in the right ventricle (RV) so that sensing or pacing of the ventricles may be performed using tip electrode 93b and/or coil electrode 93a. A ventricular cardioversion/defibrillation shock may be delivered between coil 93a and the can 60 when fibrillation or other tachyarrhythmia is detected.

The device also has an auxiliary sensing channel that comprises a channel interface 20 and a sense amplifier 21 that has its differential inputs connected to a selected electrode and to the device housing or can 60 through the switching network 70. The auxiliary sensing channel may be used to verify that a pacing pulse has achieved capture of the heart by detecting an evoked response, which is the electrical response of the heart to a pacing pulse. If the evoked response indicates that a propagating wave of depolarization has resulted, from the pacing pulse, it evidences that the paced chamber has responded appropriately and contracted. As explained below, the auxiliary sensing channel can also be used to record an electrogram or subcutaneous ECG of an intrinsic or paced beat for morphology analysis in order to detect cardiac ischemia.

The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or adjusting the pacing pulse energy by changing the pulse amplitude or pulse width. The microprocessor 10 controls the overall operation of the device in accordance with programmed instructions stored in memory. The sensing circuitry of the device generates atrial and ventricular sense signals when voltages sensed by the electrodes (i.e., electrograms) exceed a specified threshold. The controller then interprets sense signals from the sensing channels and controls the delivery of paces in accordance with a programmed pacing mode. The sense signals from any of the sensing channels of the pacemaker in FIG. 1 can be digitized and recorded by the controller to constitute an electrogram that can either be analyzed by the device itself or transmitted via the telemetry link 80 to the external programmer 300.

In the embodiment illustrated in FIG. 1, an auxiliary sensing channel is provided where the differential inputs of sensing amplifier 21 may be connected to a selected electrode and the can 60 by means of switch matrix 70 in order to record an electrogram signal for morphology analysis. The device may also have multiple auxiliary sensing channels for recording electrograms or subcutaneous ECG's having different sensing vectors simultaneously. Morphological changes in a recorded electrogram indicative of ischemia may be more easily detected in an electrogram obtained from a unipolar electrode with a large surface area rather than a conventional bipolar sensing/pacing electrode. It is therefore preferable for the auxiliary sensing channel to employ unipolar sensing such that the sensing vector is between the unipolar electrode and the device housing or can (or another distantly disposed electrode or electrodes). A large unipolar electrode "sees" a larger volume of the myocardium, and changes in the depolarization pattern of the ventricles will be more readily reflected in an electrogram generated by the electrode during a ventricular beat. A convenient electrode for this purpose is the coil electrode that the device normally uses for delivering cardioversion/defibrillation shocks. An electrogram signal suitable for morphology analysis may also be obtained by switching the auxiliary sensing channel to use one or more subcutaneous electrodes such as subcutaneous electrode 56, where the electrogram thus recorded is referred to as a subcutaneous ECG. The switch matrix also allows different sensing vectors to be used for recording the electrogram.

2. Detection and Characterization of Ischemia

An electrogram or subcutaneous ECG can be recorded of an intrinsic beat or of an evoked response to a pace and used to detect cardiac ischemia. In order to detect a change indicative of cardiac ischemia, the controller is programmed to analyze the recorded electrogram of an evoked response or an intrinsic beat and look for a "current of injury." When the blood supply to a region of the myocardium is compromised, the supply of oxygen and other nutrients can become inadequate for enabling the metabolic processes of the cardiac muscle cells to maintain their normal polarized state. An ischemic region of the heart therefore becomes abnormally depolarized during at least part of the cardiac cycle and causes a current to flow between the ischemic region and the normally polarized regions of the heart, referred to as a current of injury. A current of injury may be produced by an infarcted region that becomes permanently depolarized or by an ischemic region that remains abnormally depolarized during all or part of the cardiac cycle. A current of injury results in an abnormal change in the electrical potentials measured by either a surface electrocardiogram or an intracardiac electrogram. If the abnormal depolarization in the ventricles lasts for the entire cardiac cycle, a zero potential is measured only when the rest of the ventricular myocardium has depolarized, which corresponds to the time between the end of the QRS complex and the T wave in an electrogram and is referred to as the ST segment. After repolarization of the ventricles, marked by the T wave in an electrogram, the measured potential is influenced by the current of injury and becomes shifted, either positively or negatively depending upon the location of the ischemic or infarcted region, relative to the ST segment. Traditionally, however, it is the ST segment that is regarded as shifted when an abnormal current of injury is detected by an electrogram or electrocardiogram. A current injury produced by an ischemic region that does not last for the entire cardiac cycle may only shift part of the ST segment, resulting in an abnormal slope of the segment. A current of injury may also be produced when ischemia causes a prolonged depolarization in a ventricular region which results in an abnormal T wave as the direction of the wave of repolarization is altered.

Figure 2:
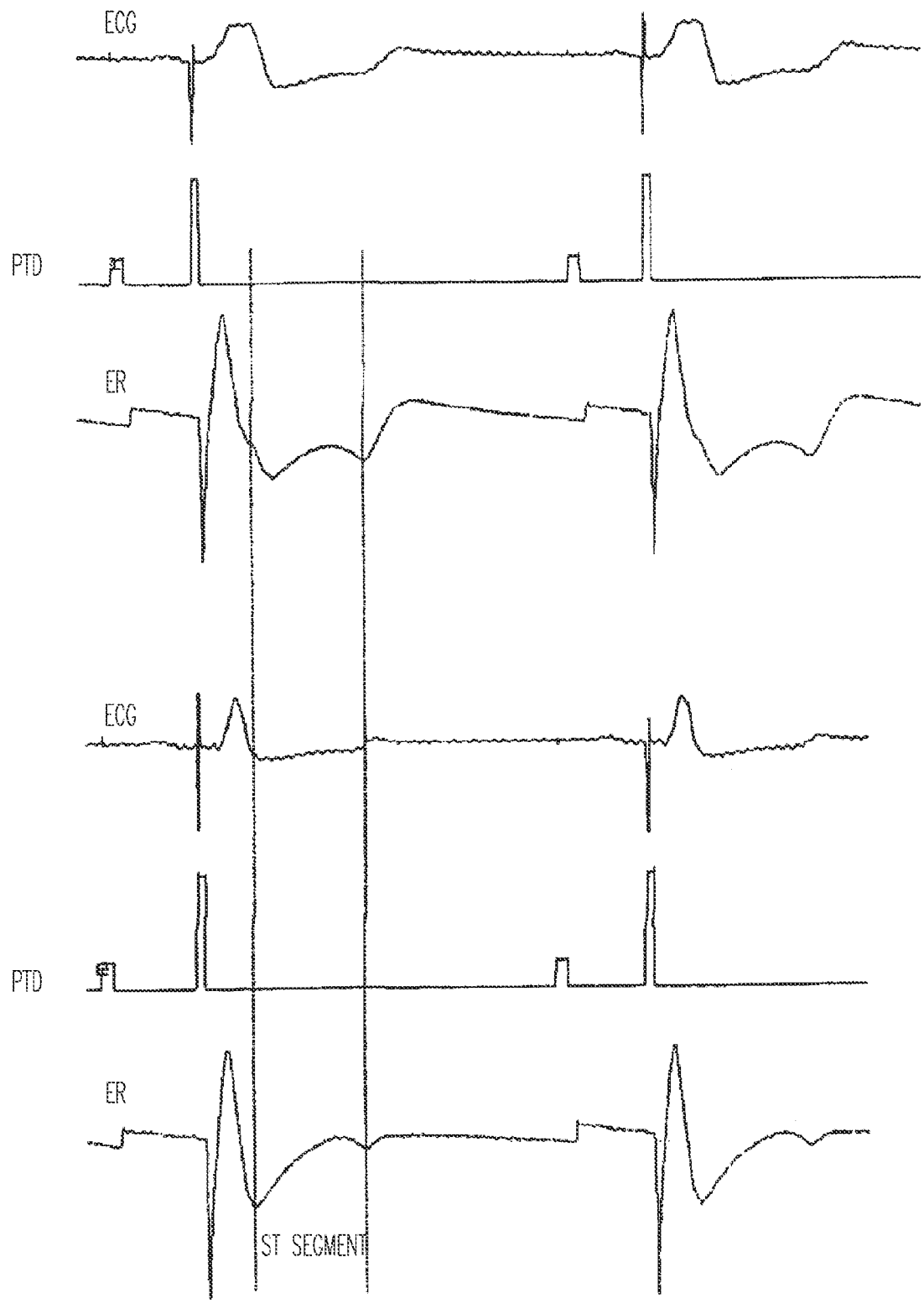
FIG. 2 illustrates ischemic changes in a recorded electrogram.

In order to detect a change in an electrogram indicative of ischemia, a recorded electrogram is analyzed and compared with a reference electrogram, which may either be a complete recorded electrogram or particular reference values representative of an electrogram. Because certain patients may always exhibit a current of injury in an electrogram (e.g., due to CAD or as a result of electrode implantation), the controller is programmed to detect ischemia by looking for an increased current of injury in the recorded electrogram as compared with the reference electrogram, where the latter may or may not exhibit a current of injury. FIG. 2 shows examples of evoked response data for two cases labeled A and B, where A is the baseline reference and B is during an acute ischemic episode. A surface electrocardiogram labeled ECG, a pacing timing diagram labeled PTD, and an electrogram labeled ER are illustrated for each case. The ST segment of the electrogram for case B is seen to have a different amplitude and slope as compared with the amplitude and slope of the ST segment of the electrogram for case A. One way to look for an increased current of injury in the recorded electrogram is to compare the ST segment amplitude and/or slope with the amplitude and slope of a reference electrogram. Various digital signal processing techniques may be employed for the analysis, such as using first and second derivatives to identify the start and end of an ST segment. Other ways of looking for a current injury may involve, for example, cross-correlating the recorded and reference electrograms to ascertain their degree of similarity. The electrogram could be implicitly recorded in that case by passing the electrogram signal through a matched filter that cross-correlates the signal with a reference electrogram. The ST segment could also be integrated, with the result of the integration compared with a reference value to determine if an increased current of injury is present. Another indicator of cardiac ischemia in electrograms or subcutaneous ECG's recorded with different sensing vectors is a shift in the dominant orientation or axis.

An increase in sympathetic activity may be indicative of the metabolic stress associated with cardiac ischemia. One means by which increased sympathetic activity may be detected is via spectral analysis of heart rate variability. Heart rate variability refers to the variability of the time intervals between successive heart beats during a sinus rhythm and is primarily due to the interaction between the sympathetic and parasympathetic arms of the autonomic nervous system. Spectral analysis of heart rate variability involves decomposing a signal representing successive beat-to-beat intervals into separate components representing the amplitude of the signal at different oscillation frequencies. It has been found that the amount of signal power in a low frequency (LF) band ranging from 0.04 to 0.15 Hz is influenced by the levels of activity of both the sympathetic and parasympathetic nervous systems, while the amount of signal power in a high frequency band (HF) ranging from 0.15 to 0.40 Hz is primarily a function of parasympathetic activity. The ratio of the signal powers, designated as the LF/HF ratio, is thus a good indicator of the state of autonomic balance, with a high LF/HF ratio indicating increased sympathetic activity. An LF/HF ratio which exceeds a specified threshold value may be taken as an indicator that cardiac function is not adequate. A cardiac rhythm management device can be programmed to determine the LF/HF ratio by analyzing data received from its atrial or ventricular sensing channels. The intervals between successive atrial or ventricular senses, referred to as beat-to-beat or BB intervals, can be measured and collected for a period of time or a specified number of beats. The resulting series of BB interval values is then stored as a discrete signal and analyzed to determine its energies in the high and low frequency bands as described above. Techniques for estimating the LF/HF ratio based upon interval data are described in commonly assigned U.S. patent application Ser. No. 10/436,876 filed May 12, 2003, and U.S. Ser. No. 10/669,170 filed Sep. 23, 2003, the disclosures of which are hereby incorporated by reference.

Figure 3:
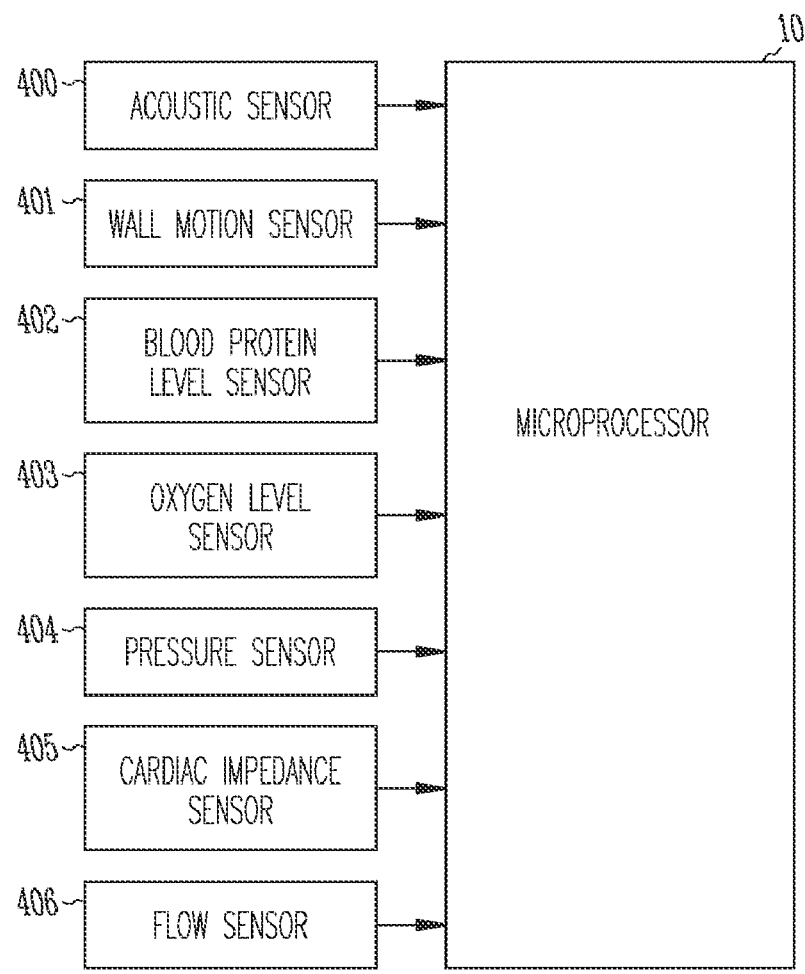
FIG. 3 illustrates additional sensing modalities that may be incorporated into the implantable device.

FIG. 3 illustrates other sensing modalities that may be incorporated into the implantable device in order to measure or detect parameters associated with cardiac ischemia. An acoustic sensor 400 (which can be implemented as an accelerometer) may be used to detect abnormal heart sounds associated with cardiac ischemia such as a third heart sound. A wall motion sensor 401 (such as an ultrasonic transducer) may be used to detect abnormal wall motion associated with cardiac ischemia such as akinesis. A blood protein level sensor 402 may be provided to determine the level of blood protein markers that are released into the blood when cardiac damage occurs such as creatinine kinase and/or troponin, where sensor comprises chemical transducers specific for each marker A chemical transducer may also be used to measure levels of blood electrolytes associated with cardiac ischemia. An oxygen level sensor 403 may be used to determine the oxygen content of the blood, and hemodynamic parameters that can be affected by cardiac ischemia such as cardiac output and pressure may be measured by pressure sensor 404, cardiac impedance sensor 405, or flow sensor 406.

Any, all, or some of the ischemia parameters discussed above may be used to detect cardiac ischemia. In order to evaluate multiple ischemia parameter values, a plurality of such parameters are mapped into a composite ischemia function. The composite ischemia function may also be a function of both a plurality of ischemia parameter values and of the times at which the ischemia parameter values were measured or otherwise collected.

In one embodiment, the composite ischemia function is a numerically-valued function of the plurality of ischemia parameters that can be compared to a threshold value to determine if cardiac ischemia is deemed to be present. An example of such a composite ischemia function is a multilinear function that is a weighted sum or average of a number of different parameters associated with cardiac ischemia:

$$\mathrm{CompIschemFunc} = \Sigma w_i P_i \text{ for } i=1 \text{ through } N$$

where CompIschemFunc is the composite ischemia function, N is the number of ischemia parameters, $P_i$ is the $i^{th}$ ischemia parameter, and $w_i$ is the weighting coefficient associated with $P_i$. The ischemia parameters may be measured values (e.g., LF/HF ratio, blood pressure, cardiac output, blood protein marker level) or an integer value representing the presence or absence of a particular event or condition (e.g., a measurable parameter value above or below a specified threshold, presence of a third heart sound, ST segment depression). The weighting coefficients may be positive in the case of a parameter that is positively correlated with cardiac ischemia or negative in the case of a parameter that is negatively correlated with cardiac ischemia. The optimal weighting coefficients for predicting cardiac ischemia with a particular sensitivity and/or specificity will generally vary from patient to patient. Optimal weighting coefficients may be determined for an individual patient from a history of how the parameters vary in relation to episodes of known cardiac ischemia as determined by clinical testing. For example, a regression analysis may be performed to select the weighting coefficients that most reliably predict ischemia. Determination of optimal weighting coefficients may be performed by code executed by the controller of the implantable device or by, for example, an external programmer using a downloaded history of parameter values.

In another embodiment, the composite ischemia function is a vector-valued function of the ischemia parameter values, where the components of the function may be compared with multiple specified threshold values in order to both detect and characterize cardiac ischemia. A vector-valued composite ischemia function may be used, for example, to assess the severity, anatomical location, or other characteristic of the ischemia.

The mapping of parameter values to the composite ischemia function, whether numerically-valued, or vector-valued, may be implemented as code executed by the device controller using an explicit mapping function (e.g., a weighed sum of parameter values) or as a table stored in memory that associates different sets of parameter values with a particular value of the composite ischemia function. A table may be derived from historical data in a similar manner to that described above for determining optimal weighting coefficients.

3. Device Response to Detection of Ischemia

If a change in ischemia parameters indicates detection or a particular characterization of cardiac ischemia, the change may be logged as a clinically significant event in the implantable device's memory. The event log and/or the recorded electrogram exhibiting the ischemia may then be later downloaded to a clinician for analysis via an external programmer. The clinician is then able to use this information in making subsequent treatment decisions. If a remote monitoring unit is present, the device may also be programmed to transmit an alarm message to a patient management server via a network.

Cardiac ischemia may also affect what is the optimum type of therapy that should be delivered to a patient. The device may therefore be configured to change its operating behavior upon detection of cardiac ischemia by altering the therapy it is normally configured to deliver or by initiating delivery of a therapy specifically to treat the ischemia. If the detected cardiac ischemia is further characterized with a vector-valued composite ischemia function, the change in operating behavior may also be made to depend upon the components of the vector. In one embodiment, an implantable device is equipped with a therapy channel for delivering therapy to the heart (e.g., bradycardia pacing, CRT, ATP, shock therapy, and/or drug therapy), one or more sensing channels for sensing cardiac electrical activity, and a controller for controlling the delivery of therapy in response to the sensed cardiac electrical activity. As described above, the device may also have one or more sensing modalities in addition to the sensing channel(s) for measuring or detecting parameters associated with cardiac ischemia. Such parameters may include a detected current of injury in a recorded electrogram, a detected third heart sound, an abnormal heart sound, a detected level of a blood protein marker associated with cardiac ischemia, a detected level of sympathetic activity as computed from heart rate variability, an oxygen content of the blood as sensed by an oximeter, abnormal heart wall motion as sensed by a wall motion sensor, or a hemodynamic parameter that can be affected by cardiac ischemia as may be measured by a pressure, cardiac impedance, or flow sensor. The controller is programmed to compute a composite ischemia function from two or more parameters associated with cardiac ischemia as detected or measured by the sensing channel(s) or one or more additional sensing modalities and to adjust the manner in which the therapy is delivered in accordance therewith.

In one embodiment, the composite ischemia function is a numerically-valued function, such as a weighted sum of the measured or detected parameters associated with cardiac ischemia, that is compared with a specified threshold value in order to detect ischemia. In another embodiment, the composite ischemia function is a vector-valued function that is compared with a plurality of specified threshold values corresponding to the components of the vector-valued function in order to detect and characterize the ischemia. The controller may then be programmed adjust the manner in which therapy is delivered in accordance with the characterization of the ischemia as represented by the vector-valued composite ischemia function. As described below, the adjustments to the manner in which therapy is delivered may be effected by the controller taking one or more of the following actions upon detection of cardiac ischemia or upon a particular characterization of cardiac ischemia: 1) modifying the behavior of the device in delivering pacing therapy in a rate-adaptive mode by taking one or more actions selected from a group that includes discontinuing rate-adaptive pacing, decreasing the specified maximum sensor-indicated rate, and adjusting a response factor of a rate-response curve so that a particular exertion level particular is mapped to a lower sensor-indicated rate if cardiac ischemia is detected, 2) decreasing a maximum tracking rate that limits the rate at which ventricular paces can be delivered in response to atrial senses, 3) decreasing the atrio-ventricular interval used to deliver pacing therapy in accordance with an atrial tracking or AV sequential pacing mode, 4) lowering the lower rate limit used to deliver paces, 5) changing the pacing vector used to deliver paces, 6) initiating or increasing hysteresis with respect to the lower rate limit upon detection of cardiac ischemia, 7) switching from a ventricular pacing mode to a non-ventricular pacing mode, 8) more preferentially delivering shock therapy as opposed to ATP upon by lowering the fibrillation detection rate, 9) treating all tachyarrhythmias with shock therapy upon detection of cardiac ischemia, or 10) modifying one or more ATP pacing parameters selected from a group that includes pacing rate, pacing site, and pacing vector upon detection of cardiac ischemia.

The most common condition for which pacemakers are used is the treatment of bradycardia where the intrinsic heart rate is too slow, due usually to AV block or sinus node dysfunction. In chronotropically competent patients (i.e., those patients whose atrial rhythm is responsive to metabolic demand) in need of ventricular pacing, atrial triggered modes such as DDD or VDD are desirable because they allow the pacing to track the physiologically normal atrial rhythm, which causes cardiac output to be responsive to the metabolic needs of the body. In pacemaker patients who are chronotropically incompetent (e.g., sinus node dysfunction) or in whom atrial tracking modes such as DDD and VDD are contraindicated due to atrial arrhythmias, the heart rate is dictated solely by the pacemaker in the absence of faster intrinsic cardiac activity. That pacing rate is determined by the programmed escape intervals of the pacemaker and is referred to as the lower rate limit or LRL. Pacing the heart at a fixed rate as determined by the LRL setting of the pacemaker, however, does not allow the heart rate to increase with increased metabolic demand. Rate-adaptive pacemakers have therefore been developed where the patient's metabolic demand is estimated with an exertion level sensor such as an accelerometer or minute-ventilation sensor. The sensed exertion level is then mapped to a sensor-indicated rate that becomes the lower rate limit for the pacemaker.

Rate-adaptive pacing is generally considered to be contraindicated for patients with known coronary artery disease (CAD) since the increase in heart rate brought about by rate-adaptive pacing also increases the oxygen demand of the heart. If the heart becomes ischemic due to insufficient blood flow in the face of increased oxygen demand, chest pain (angina pectoris) or triggering of an arrhythmia may result. For the same reasons, atrial tracking ventricular pacing modes may also be contraindicated in certain patients where cardiac ischemia results from atrial tracking pacing at high rates. Accordingly, a pacemaker with the capability of detecting cardiac ischemia may be configured to adjust its pacing mode upon such detection.

In an atrial tracking mode, for example, one or both ventricles are paced after expiration of a programmed atrio-ventricular interval if no preceding ventricular sense occurs, where the atrio-ventricular interval begins with an atrial sense. The pacing of the ventricles thus tracks the intrinsic atrial rate which, in a chronotropically competent patient, is responsive to metabolic demand. For safety reasons, a maximum tracking rate is usually programmed into an atrial tracking mode that limits the rate at which the ventricles can be paced regardless of the atrial rate. When ischemia is detected by the pacemaker, the controller may be programmed to automatically decrease the maximum tracking rate so that the ventricles are paced at that rate even if the intrinsic atrial rate is higher. Decreasing of the maximum tracking rate may thus prevent exacerbation of the ischemia from pacing at too high a rate. The decreased maximum tracking rate may be a specified value or an algorithmically determined value.

Figure 4:
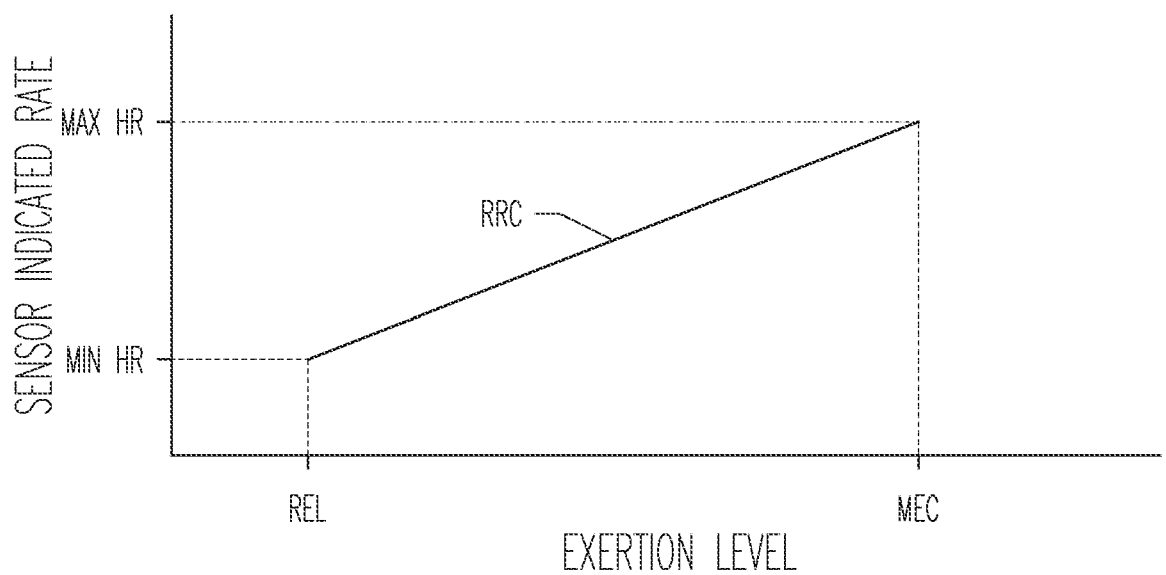
FIG. 4 is a diagram of a single-slope rate response curve.

Automatic adjustment of the maximum pacing rate when cardiac ischemia is detected may also be employed in rate-adaptive pacing. In a rate-adaptive pacemaker operating in a ventricular pacing mode, the LRL is adjusted in accordance with exertion level measurements such as from an accelerometer or minute ventilation sensor in order for the heart rate to more nearly match metabolic demand. The adjusted LRL is then termed the sensor-indicated rate. The responsiveness of a rate-adaptive pacemaker is controlled in accordance with a rate-response curve RRC such as shown in FIG. 4. Other embodiments may use a dual-slope curve or a non-linear curve. A change in exertion level as determined from a minute ventilation measurement causes a proportional change in the sensor indicated rate in accordance with the slope of the curve, termed the response factor RF. The sensor indicated rate is then used as a lower rate limit (LRL) by the pacemaker to pace the heart in accordance with a programmed pacing mode, where the LRL is the rate at which the heart is paced in the absence of faster intrinsic activity. As shown in the figure, the rate response curve maps a resting exertion level REL to a minimum sensor indicated rate MinHR which corresponds to the minimum LRL that is to be used by the pacemaker. The maximum sensor indicated rate MaxHR is the maximum rate at which the pacemaker is allowed to pace the heart and is mapped to by the rate response curve from the maximum exertion level the patient is expected to be able to reach, referred to as the maximum exercise capacity MEC. When cardiac ischemia is detected from a recorded electrogram, the controller may be programmed to decrease the maximum allowable sensor-indicated rate MaxHR. The response factor of the rate response curve can also be adjusted to map a given exertion level to a lower sensor-indicated rate if cardiac ischemia is detected. In another embodiment, the device may be configured to simply discontinue rate-adaptive pacing upon detection of cardiac ischemia.

A pacemaker may be configured to alter its pacing behavior in other ways upon detection of cardiac ischemia. For example, the LRL may be lowered to a specified value or an algorithmically determined value. The device could also switch to a mode that decreases the extent of ventricular pacing and encourages intrinsic beats such as one employing hysteresis or a mode with greater hysteresis than the device's normal pacing mode. The device could also switch from a ventricular pacing mode to a non-ventricular pacing mode such as AAI. The device could also utilize the switch matrix 70 to change the pacing vector used to deliver pacing such as by switching to or from bipolar and unipolar pacing (or switching to other pacing configurations using multi-polar leads) or to change the pacing site (e.g., switching from right ventricular pacing to biventricular pacing). The device could also be configured to shorten the AV delay interval used to deliver ventricular paces in atrial tracking or AV sequential pacing modes in order to increase the duration of ventricular diastole during which the myocardium is perfused from the coronary arteries.

Patients with atrial arrhythmias will often have irregular ventricular intervals, because rapid atrial depolarizations may enter the refractory period of the atrio-ventricular node, leading to irregular ventricular intervals. Some patients with atrial arrhythmias and implanted pacemakers/ICDs will have their devices programmed to smooth the ventricular rate by dynamically adjusting the ventricular pacing rate to a minimally overdriven rate, termed ventricular rate regularization. Similarly, some atrial arrhythmia termination algorithms will preferentially pace the atrium a certain number of beats above the intrinsic atrial rate, termed atrial preference pacing. (See, e.g., U.S. Pat. No. 6,285,907 assigned to Cardiac Pacemakers, Inc. and hereby incorporated by reference.) The ischemia sensor can be used to adapt the upper rate of these algorithms, preventing the dynamically adapted rate from causing ischemia.

The device may also be configured to modify its behavior in delivering anti-tachyarrhythmia therapy (i.e., ATP and shock therapy) in response to detection of ischemia. In ATP, the heart is competitively paced with one or more pacing pulses in an effort to interrupt the reentrant circuit causing the tachycardia. Shock therapy terminates a tachyarrhythmia by depolarizing all of the myocardium simultaneously and rendering it refractory. A measured heart rate is classified as a tachycardia when the rate is in a tachycardia zone, defined as a range of rates above a tachycardia detection rate (TDR) but below a fibrillation detection rate (FDR). A measured heart rate above the FDR, on the other hand, is in the fibrillation zone and is treated with shock therapy. In most devices, a tachyarrhythmia with a heart rate in the tachycardia zone is treated with ATP therapy in order to avoid an unnecessary painful shock to the patient, and a defibrillation shock is delivered if the pacing fails to terminate the tachyarrhythmia. When cardiac ischemia is detected, the device may be configured to more preferentially deliver shock therapy by, for example, lowering the FDR or treating all tachyarrhythmias with shock therapy. The device may also modify ATP pacing parameters such as pacing rate, pacing site, or pacing vector. The device may also increase the shock energy delivered above the programmed value, as it is known that arrhythmias typically have higher defibrillation thresholds when cardiac ischemia is present.

The device may also be equipped with drug delivery capability, with the device configured to deliver a dose of medication (e.g., a thrombolytic) when cardiac ischemia is detected in the manner described herein. A drug delivery system 500 is shown in FIG. 1 as interfaced to the device controller. Such a drug delivery system may be either an implantable system or an external drug delivery system such as described in U.S. Pat. No. 6,361,522, assigned to Cardiac Pacemakers, Inc. and hereby incorporated by reference.

Figure 5:
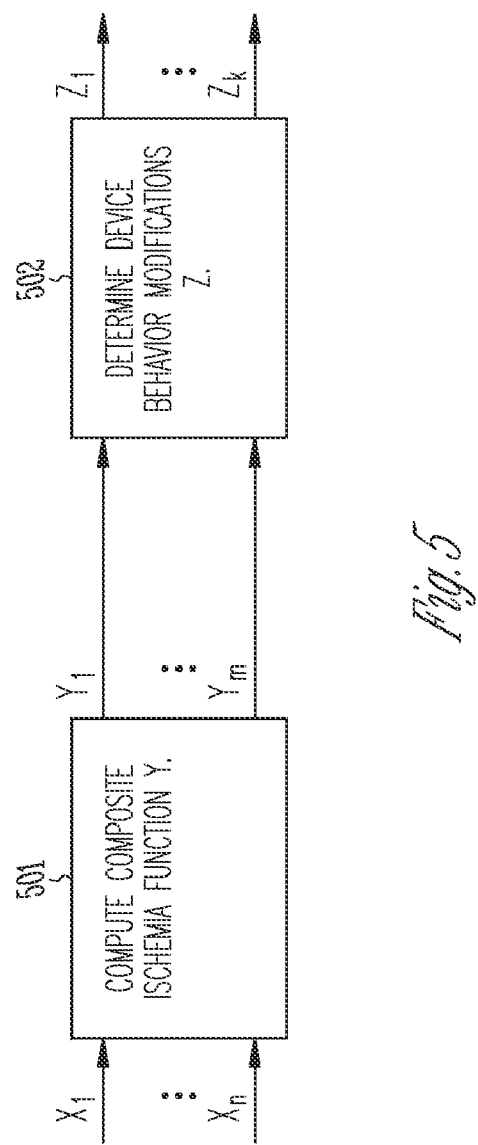
FIG. 5 illustrates a vector-valued composite ischemia function and therapy adjustments made in accordance therewith.

As described above, a plurality of ischemia parameters may be collected by the implantable device and used to compute a composite ischemia function. FIG. 5 illustrates an exemplary algorithm that may be implemented in the programming of an implantable device for responding to cardiac ischemia with appropriate therapy modifications. A vector-valued composite ischemia function is computed by a function mapper 501 from n ischemia parameters designated $X_1$ through $X_n$. The composite ischemia function has m components designated $Y_1$ through $Y_m$ that serve to detect and characterize the ischemia in accordance with their particular values. The components of composite ischemia function are then mapped by a function mapper 502 to k device behavior modifications designated $Z_1$ through $Z_k$. Such device behavior modifications may be any of those discussed above that affect the manner in which therapy is delivered by the device. The device may thus be configured to modify its behavior in a way that depends upon the characterization of the ischemia represented by the vector-valued composite ischemia function.

Although the invention has been described in conjunction with the foregoing specific embodiment, many alternatives, variations, and modifications will be apparent to those of ordinary skill in the art upon reading and understanding the teaching set forth herein. Such alternatives, variations, and modifications are intended to fall within the scope of the following appended claims.

What is claimed is:

1. A cardiac device, comprising:
   one or more sensing channels for sensing cardiac activity;
   one or more physiological sensors for sensing one or more variables related to cardiac ischemia;
   a therapy channel for delivering therapy to the heart;
   a controller for controlling the delivery of therapy in response to the sensed cardiac activity; and,
   wherein the controller is programmed to:
   collect a plurality of parameters associated with cardiac ischemia from the sensing channels and/or physiological sensors, where the plurality of parameters are designated $X_1$ through $X_n$;
   compute a vector-valued composite ischemia function that maps the plurality of parameters $X_1$ through $X_n$ to a vector with a plurality of components designated $Y_1$ through $Y_m$ that characterize the ischemia by: performing a regression analysis of historical values of the parameters and episodes of known ischemia, determining weighting coefficients from said analysis for each component of the vector-valued composite ischemia function, and computing each component of the vector-valued composite ischemia function as a weighted sum of one or more of the plurality of parameters using said weighting coefficients; and,
   adjust the manner in which the therapy is delivered by mapping the vector-valued composite ischemia function to a plurality of device behavior modifications designated $Z_1$ through $Z_k$.

2. The device of claim 1 further comprising one or more sensing modalities in addition to the one or more sensing channels for measuring or detecting a plurality of parameters associated with cardiac ischemia.

3. The device of claim 1 wherein the controller is programmed to compute at least one component of the composite ischemia function as a numerically-valued function and to compare that component of composite ischemia function with a specified threshold value in order to detect ischemia.

4. The device of claim 3 wherein the controller is further programmed to compute at least one component of the composite ischemia function as a weighted sum of the measured or detected parameters associated with cardiac ischemia.

5. The device of claim 1 wherein the controller is programmed to compare the composite ischemia function with a plurality of specified threshold values corresponding to the components of the vector-valued function in order to detect and characterize the ischemia.

6. The device of claim 5 wherein the controller is programmed to adjust the manner in which therapy is delivered in accordance with the characterization of the ischemia as represented by the vector-valued composite ischemia function.

7. The device of claim 1 further comprising:
an exertion level sensor;
wherein the therapy channel is a pacing channel and the controller is programmed to:
deliver pacing therapy in accordance with a rate-adaptive pacing mode in which a sensed exertion level is mapped to a particular sensor-indicated rate with a rate-response curve and the sensor-indicated rate is limited to a specified maximum sensor-indicated rate; and,
modify the behavior of the device in delivering pacing therapy upon detection of ischemia by taking one or more actions selected from a group that includes discontinuing rate-adaptive pacing, decreasing the specified maximum sensor-indicated rate, and adjusting a response factor of a rate-response curve so that a particular exertion level is mapped to a lower sensor-indicated rate if cardiac ischemia is detected.

8. The device of claim 1 wherein the therapy channel is a pacing channel for pacing a ventricle and the controller is programmed to:
deliver pacing therapy in accordance with an atrial tracking mode such that a ventricular pace is delivered after expiration of an atrio-ventricular interval without a ventricular sense, the atrio-ventricular interval being started by an atrial sense; and,
decrease a maximum tracking rate that limits the rate at which ventricular paces can be delivered in response to atrial senses if cardiac ischemia is detected.

9. The device of claim 1 wherein the therapy channel is a pacing channel for pacing a ventricle and the controller is programmed to:
deliver pacing therapy in accordance with an atrial tracking or AV sequential pacing mode such that a ventricular pace is delivered after expiration of an atrio-ventricular interval without a ventricular sense, the atrio-ventricular interval being started by an atrial sense or pace; and;
decrease the atrio-ventricular interval upon detection of cardiac ischemia.

10. The device of claim 1 wherein the therapy channel is a pacing channel for pacing a ventricle and the controller is programmed to:
deliver pacing therapy in accordance with a specified lower rate limit (LRL); and,
lower the LRL upon detection of cardiac ischemia.

11. The device of claim 1 wherein the therapy channel is a pacing channel for pacing a ventricle and the controller is programmed to:
deliver pacing therapy with a specified pacing vector; and,
change the pacing vector upon detection of cardiac ischemia.

12. The device of claim 1 wherein the therapy channel is a pacing channel for pacing a ventricle and the controller is programmed to:
deliver pacing therapy in accordance with a specified lower rate limit (LRL); and,
initiate or increase hysteresis with respect to the LRL upon detection of cardiac ischemia.

13. The device of claim 1 wherein the therapy channel is a pacing channel and the controller is programmed to:
deliver pacing therapy to a ventricle in accordance with a programmed mode; and,
switch from a ventricular pacing mode to a non-ventricular pacing mode upon detection of cardiac ischemia.

14. The device of claim 1 wherein the therapy channel is a pacing channel and the controller is programmed to:
deliver pacing therapy to a ventricle in accordance with a programmed ventricular rate regularization mode; and,
adapt the upper rate of the ventricular rate regularization mode upon detection of cardiac ischemia.

15. The device of claim 1 wherein the therapy channel is a pacing channel and the controller is programmed to:
deliver pacing therapy in accordance with a programmed atrial preference pacing mode; and,
adapt the upper rate of the atrial preference pacing mode upon detection of cardiac ischemia.

16. The device of claim 1 wherein the therapy channels include a pacing channel and a shock channel for delivering ATP and shock therapy, respectively, and wherein the controller is programmed to:
deliver shock therapy if a tachyarrhythmia above a fibrillation detection rate (FDR) is detected and deliver ATP if a tachyarrhythmia below the FDR is detected; and, more preferentially deliver shock therapy upon detection of cardiac ischemia by lowering the FDR.

17. The device of claim 1 wherein the therapy channels include a pacing channel and a shock channel for delivering ATP and shock therapy, respectively, and wherein the controller is programmed to:
deliver shock therapy if a tachyarrhythmia above a fibrillation detection rate (FDR) is detected and deliver ATP if a tachyarrhythmia below the FDR is detected; and,
treat all tachyarrhythmias with shock therapy upon detection of cardiac ischemia.

18. The device of claim 1 wherein the therapy channels include a pacing channel and a shock channel for delivering ATP and shock therapy, respectively, and wherein the controller is programmed to:
deliver shock therapy if a tachyarrhythmia above a fibrillation detection rate (FDR) is detected and deliver ATP if a tachyarrhythmia below the FDR is detected; and,
modify one or more ATP pacing parameters selected from a group that includes pacing rate, pacing site, and pacing vector upon detection of cardiac ischemia.

19. The device of claim 1 wherein one or more of the parameters associated with cardiac ischemia are selected from a group that includes a detected current of injury in a recorded electrogram, a detected third heart sound, an abnormal heart sound, a detected level of a blood protein marker associated with cardiac ischemia, a detected level of a blood electrolyte associated with cardiac ischemia, a detected level of sympathetic activity as computed from heart rate variability, an oxygen content of the blood as sensed by an oximeter, abnormal heart wall motion as sensed by a wall motion sensor, and a hemodynamic parameter that can be affected by cardiac ischemia as may be measured by a pressure, cardiac impedance, or flow sensor.

20. A method, comprising:
sensing cardiac activity;
delivering therapy to the heart in response to the sensed cardiac activity;
sensing a plurality of parameters associated with cardiac ischemia;
collecting a plurality of parameters associated with cardiac ischemia from the sensing channels and/or physiological sensors, where the plurality of parameters are designated $X_1$ through $X_n$;
computing a vector-valued composite ischemia function that maps the plurality of parameters $X_1$ through $X_n$ to a vector with a plurality of components designated $Y_1$ through $Y_m$ that characterize the ischemia by: performing a regression analysis of historical values of the parameters and episodes of known ischemia, determining weighting coefficients from said analysis for each component of the vector-valued composite ischemia function, and computing each component of the vector-valued composite ischemia function as a weighted sum of one or more of the plurality of parameters using said weighting coefficients; and,
adjusting the manner in which the therapy is delivered by mapping the vector-valued composite ischemia function to a plurality of device behavior modifications designated $Z_1$ through $Z_k$.

21. The method of claim 20 wherein the parameters associated with cardiac ischemia include a parameter derived from the sensed cardiac electrical activity and a parameter derived using one or more additional sensing modalities.

22. The method of claim 20 further comprising computing at least one component of the composite ischemia function as a numerically-valued function and comparing that component of the composite ischemia function with a specified threshold value in order to detect ischemia.

23. The method of claim 22 further comprising computing at least one component of the composite ischemia function as a weighted sum of the measured or detected parameters associated with cardiac ischemia.

24. The method of claim 20 further comprising comparing the composite ischemia function with a plurality of specified threshold values corresponding to the components of the vector-valued function in order to detect and characterize the ischemia.

25. The method of claim 24 further comprising adjusting the manner in which therapy is delivered in accordance with the characterization of the ischemia as represented by the vector-valued composite ischemia function.

26. The method of claim 20 further comprising:
delivering pacing therapy in accordance with a rate-adaptive pacing mode in which a sensed exertion level is mapped to a particular sensor-indicated rate with a rate-response curve and the sensor-indicated rate is limited to a specified maximum sensor-indicated rate; and,
modifying the behavior of the method in delivering pacing therapy upon detection of ischemia by taking one or more actions selected from a group that includes discontinuing rate-adaptive pacing, decreasing the specified maximum sensor-indicated rate, and adjusting a response factor of a rate-response curve so that a particular exertion level is mapped to a lower sensor-indicated rate if cardiac ischemia is detected.

27. The method of claim 20 further comprising:
delivering pacing therapy in accordance with an atrial tracking mode such that a ventricular pace is delivered after expiration of an atrio-ventricular interval without a ventricular sense, the atrio-ventricular interval being started by an atrial sense; and,
decreasing a maximum tracking rate that limits the rate at which ventricular paces can be delivered in response to atrial senses if cardiac ischemia is detected.

28. The method of claim 20 further comprising:
delivering pacing therapy in accordance with an atrial tracking or AV sequential pacing mode such that a ventricular pace is delivered after expiration of an atrio-ventricular interval without a ventricular sense, the atrio-ventricular interval being started by an atrial sense or pace; and;
decreasing the atrio-ventricular interval upon detection of cardiac ischemia.

29. The method of claim 20 further comprising:
delivering pacing therapy in accordance with a specified lower rate limit (LRL); and,
lowering the LRL upon detection of cardiac ischemia.

30. The method of claim 20 further comprising:
delivering pacing therapy with a specified pacing vector; and,
changing the pacing vector upon detection of cardiac ischemia.

31. The method of claim 20 further comprising:
delivering pacing therapy in accordance with a specified lower rate limit (LRL); and,
initiating or increasing hysteresis with respect to the LRL upon detection of cardiac ischemia.

32. The method of claim 20 further comprising:
delivering pacing therapy to a ventricle in accordance with a programmed mode; and,
switching from a ventricular pacing mode to a non-ventricular pacing mode upon detection of cardiac ischemia.

33. The method of claim 20 further comprising:
delivering pacing therapy to a ventricle in accordance with a programmed ventricular rate regularization mode; and,
adapting the upper rate of the ventricular rate regularization mode upon detection of cardiac ischemia.

34. The method of claim 20 further comprising:
delivering pacing therapy in accordance with a programmed atrial preference pacing mode; and,
adapting the upper rate of the atrial preference pacing mode upon detection of cardiac ischemia.

35. The method of claim 20 further comprising:
delivering shock therapy if a tachyarrhythmia above a fibrillation detection rate (FDR) is detected and delivering ATP if a tachyarrhythmia below the FDR is detected; and,
more preferentially delivering shock therapy upon detection of cardiac ischemia by lowering the FDR.

36. The method of claim 20 further comprising:
delivering shock therapy if a tachyarrhythmia above a fibrillation detection rate (FDR) is detected and deliver ATP if a tachyarrhythmia below the FDR is detected; and,
treating all tachyarrhythmias with shock therapy upon detection of cardiac ischemia.

37. The method of claim 20 further comprising:
delivering shock therapy if a tachyarrhythmia above a fibrillation detection rate (FDR) is detected and deliver ATP if a tachyarrhythmia below the FDR is detected; and,
modifying one or more ATP pacing parameters selected from a group that includes pacing rate, pacing site, and pacing vector upon detection of cardiac ischemia.

38. The method of claim 20 further comprising increasing the shock energy used to deliver shock therapy upon detection of cardiac ischemia.

39. The method of claim 20 wherein one or more of the parameters associated with cardiac ischemia are selected from a group that includes a detected current of injury in a recorded electrogram, a detected third heart sound, an abnormal heart sound, a detected level of a blood protein marker associated with cardiac ischemia, a detected level of a blood electrolyte associated with cardiac ischemia, a detected level of sympathetic activity as computed from heart rate variability, an oxygen content of the blood as sensed by an oximeter, abnormal heart wall motion as sensed by a wall motion sensor, and a hemodynamic parameter that can be affected by cardiac ischemia as may be measured by a pressure, cardiac impedance, or flow sensor.

\* \* \* \* \*